United States Patent
Chau (10) Patent No.: US 10,226,120 B2
(45) Date of Patent: Mar. 12, 2019

(54) WORKSPACE FOR PERFORMING LIQUID CHROMOTOGRAPHY ANALYSIS

(71) Applicant: Quest Diagnostics Investments LLC, Madison, NJ (US)

(72) Inventor: Laura Chau, Irvine, CA (US)

(73) Assignee: QUEST DIAGNOSTICS INVESTMENTS LLC, Madison, NJ (US)

( * ) Notice: Subject to any disclaimer, the term of this patent is extended or adjusted under 35 U.S.C. 154(b) by 0 days.

(21) Appl. No.: 15/241,459

(22) Filed: Aug. 19, 2016

(65) Prior Publication Data

US 2017/0049225 A1 Feb. 23, 2017

Related U.S. Application Data

(60) Provisional application No. 62/208,150, filed on Aug. 21, 2015.

(51) Int. Cl.
| | |
|---|---|
| A47B 37/00 | (2006.01) |
| A47B 46/00 | (2006.01) |
| A47B 57/10 | (2006.01) |
| B01L 9/02 | (2006.01) |
| G01N 30/88 | (2006.01) |
| A47B 17/03 | (2006.01) |

(52) U.S. Cl.
CPC .............. *A47B 37/00* (2013.01); *A47B 46/00* (2013.01); *A47B 57/10* (2013.01); *B01L 9/02* (2013.01); *A47B 17/03* (2013.01); *A47B 2037/005* (2013.01); *G01N 2030/8881* (2013.01)

(58) Field of Classification Search
CPC ..... A47B 83/001; A47B 83/04; A47B 83/045; A47B 57/10; A47B 57/05; A47B 57/34; A47B 57/58; A47B 2083/006; A47B 47/0075; A47B 2037/005
See application file for complete search history.

(56) References Cited

U.S. PATENT DOCUMENTS

| | | | | |
|---|---|---|---|---|
| 4,736,689 A * | 4/1988 | Stanko | ............... | A47B 21/0314 108/143 |
| 4,905,609 A * | 3/1990 | Haskins | ................. | A47B 13/06 108/23 |
| 4,949,853 A * | 8/1990 | Klein | ..................... | A47B 47/02 108/180 |
| 5,231,562 A * | 7/1993 | Pierce | ..................... | A47B 21/06 108/50.02 |
| 5,645,800 A * | 7/1997 | Masterson | ......... | G01N 35/1002 422/561 |
| 6,355,165 B1 * | 3/2002 | Sutton | .................. | B01D 15/161 210/175 |
| 6,673,316 B1 * | 1/2004 | Okamoto | ............... | B01J 19/004 422/130 |
| 6,786,161 B2 * | 9/2004 | Fischer | .................... | A47B 9/18 108/50.01 |
| 7,008,599 B1 * | 3/2006 | Carlton | .................... | G01N 1/40 422/245.1 |

(Continued)

*Primary Examiner* — Hanh V Tran
(74) *Attorney, Agent, or Firm* — Foley & Lardner LLP (57) ABSTRACT

A work space apparatus for performing scientific analysis having a plurality of modules coupled to an upper region of a desk surface and a top surface coupled to and vertically above the plurality of modules. Each of the plurality of modules has a width defined by a first sidewall and second sidewall and a height that is adjustable.

14 Claims, 8 Drawing Sheets

(56) References Cited

U.S. PATENT DOCUMENTS

| | | | | |
|---|---|---|---|---|
| 7,061,605 B2* | 6/2006 | Lemmo | ............... | B01J 19/0046 |
| | | | | 356/300 |
| 7,270,785 B1* | 9/2007 | Lemme | ............... | G01N 1/312 |
| | | | | 422/537 |
| 7,303,725 B2* | 12/2007 | Reinhardt | ............... | B01L 9/52 |
| | | | | 422/63 |
| 7,378,055 B2* | 5/2008 | Lemme | ............... | G01N 1/312 |
| | | | | 422/64 |
| 7,468,161 B2* | 12/2008 | Reinhardt | ............... | B01L 9/52 |
| | | | | 422/536 |
| 2002/0011032 A1* | 1/2002 | Choi | ............... | A47B 21/00 |
| | | | | 52/27 |

* cited by examiner

WORKSPACE FOR PERFORMING LIQUID CHROMOTOGRAPHY ANALYSIS

CROSS-REFERENCE TO RELATED APPLICATIONS

This application claims priority to U.S. Provisional Application No. 62/208,150, filed Aug. 21, 2015, entitled "Workspace for Performing Liquid Chromatography Analysis," the entire contents of which are hereby incorporated by reference herein in its entirety.

FIELD

The present technology relates generally to a work space apparatus. More particularly, the disclosure relates to a work space apparatus for performing scientific analysis, for example, chromatography.

BACKGROUND INFORMATION

Scientific analysis often requires a unique work space apparatus for the various analysis steps to be performed. For example, chromatography is a set of laboratory techniques that are used for separating a mixture. Through chromatography techniques, various constituents of the mixture are separated, for example, by causing the various constituents to travel at different speeds. The separation techniques may be used to distinguish the various constituents among each other to identify the mixture. A chromatography apparatus includes multiple components such as pumps, detectors, solvents, waste collectors that must be housed together in a work space. Currently available work spaces do not provide optimal and efficient areas for users.

SUMMARY

Disclosed herein is a work space for performing scientific analysis, for example, liquid chromatography.

In a first aspect, disclosed is a work space apparatus for performing scientific analysis having a plurality of modules coupled to an upper region of a desk surface and a top surface coupled to and vertically above the plurality of modules. Each of the plurality of modules has a width defined by a first sidewall and second sidewall and a height that is adjustable.

The height of each of the plurality of modules can be defined by at least a first shelf board that is removable from the apparatus. The first sidewall can have at least a first groove and the second sidewall can have at least a second groove. The first groove and the second groove can be positioned directly opposite one another forming a first pair of grooves. The at least a first shelf board can have a first edge that mates with the first groove in the first sidewall and a second edge that mates with the second groove in the second side wall. The at least a first shelf board can be slidingly removable from the first pair of grooves and slidingly insertable into a second pair of grooves. The second pair of grooves can be positioned in the first and second sidewall a distance above or below the first pair of grooves.

The apparatus can further include a shelf coupled below the desk surface. The shelf can be a pullout shelf having a pair of tracks for stowing the pullout shelf beneath the desk surface and for extending the pullout shelf in a first direction beyond at least one dimension of the desk surface. The apparatus can further include a utility tray coupled to the desk surface and movable in a second direction. The first direction and the second direction can be different from each other. The apparatus can further include an electrical panel extending vertically downward from the desk surface. The apparatus can further include at least one power supply or at least one power electronic unit housed within the electrical panel and a plurality of vent holes for dissipating heat from the at least one power supply or at least one power electronic unit. The desk surface can include at least one cutout for facilitating an electrical connection of equipment placed within one of the plurality of modules. The apparatus can further include a screen monitor housed on a side surface of the work space apparatus. The apparatus can further include a flip tray hinged to the desk surface. The flip tray can serve as a protective covering for the screen monitor. The apparatus can include a lower support coupled to the desk surface. The lower support can be coupled to casters having a wheel lock.

The apparatus can be configured to house a chromatography apparatus, such as a liquid chromatography apparatus. The chromatography apparatus can include a plurality of system components, each of the system components housed within its respective one of the plurality of modules.

In an interrelated aspect, disclosed is a method for performing chromatography analysis using a work space apparatus. The method includes supporting a plurality of modules on an upper region of a desk surface. The method includes storing at least a first liquid reservoir within a utility tray coupled to the upper region of the desk surface behind the plurality of modules. The method includes housing at least a first component of a chromatography system within a first of the plurality of modules. The first of the plurality of modules has a height that is adjustable. The method can further include adjusting the height of the first of the plurality of modules. A shelf can be coupled to the desk surface. The shelf can be a pullout shelf for extending in a first direction beyond at least one dimension of the desk surface. The utility tray can be movable relative to the desk surface. The utility tray can move in a direction opposite the first direction. The chromatography system can be a liquid chromatography system.

In some variations, one or more of the following can optionally be included in any feasible combination in the above methods, apparatus, devices, and systems. More details of the devices, systems, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively, but are intended to be illustrative. Also, relative placement of features and elements may be modified for the purpose of illustrative clarity. It is to be understood that devices described herein may include features not necessarily depicted in each figure.

DETAILED DESCRIPTION

Work spaces for performing scientific analyses may vary. As an example, chromatography techniques include many sequential processing steps using various system components. The system components of chromatography systems including, but not limited to liquid chromatography (LC), high-performance liquid chromatography (HPLC), normal-phase HPLC (NP-HPLC), reversed-phase HPLC, partition chromatography, size-exclusion chromatography (SEC), ion-exchange chromatography, bioaffinity chromatography, displacement chromatography, gas chromatography (GC), etc., can include multiple solvent reservoirs, pumping devices, analytical columns, detectors (such as UV-Vis absorbance detector or mass spectrometer), data acquisition machines, and collectors for waste and/or fractions. Described herein is a work space apparatus specially adapted for use in a laboratory that supports and organizes the various components in laboratory analyses systems to enhance optimal results.

Figure 1:
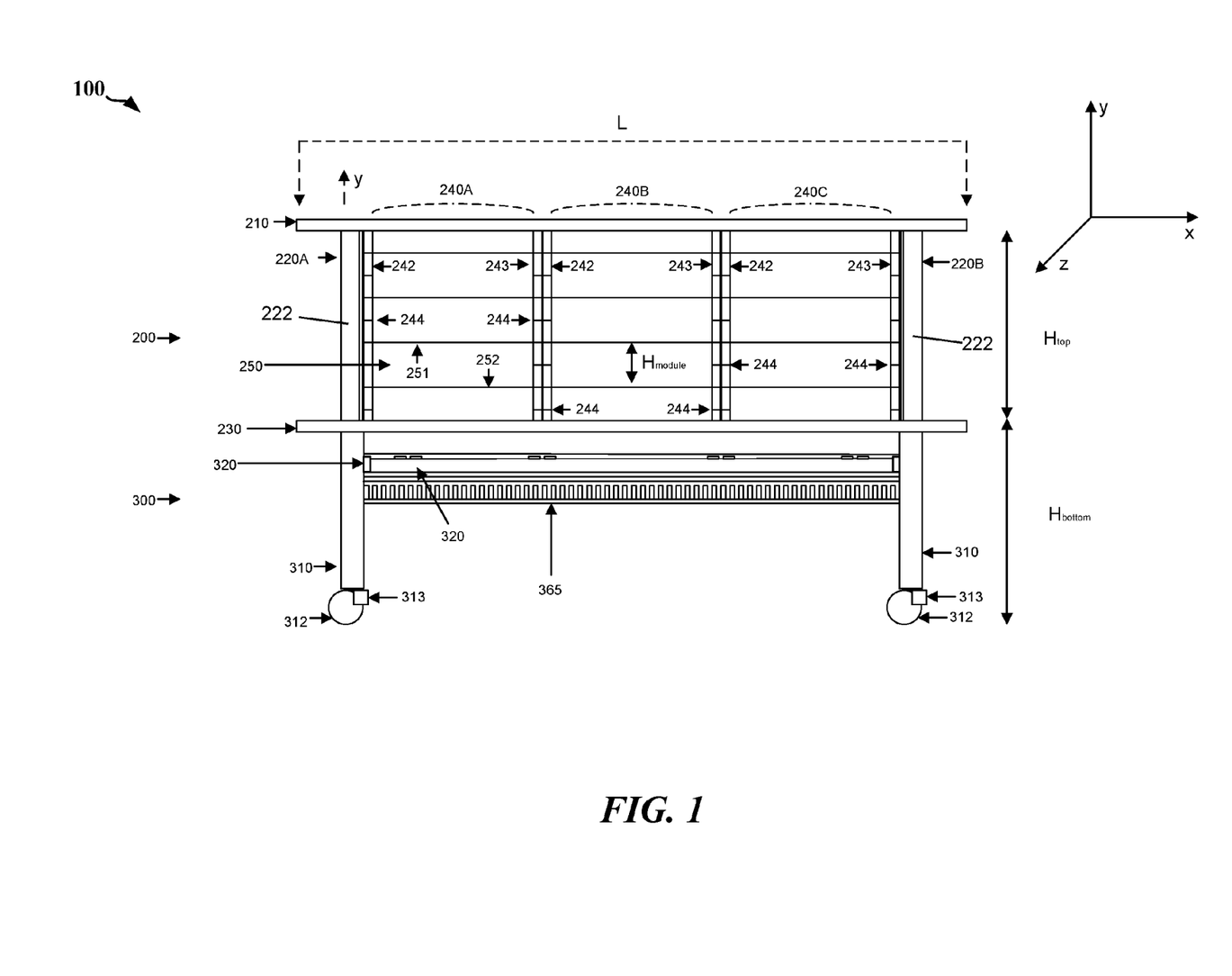
FIG. 1 illustrates a front view of an implementation of a work space apparatus for performing laboratory analyses.

Referring now to the drawings, FIG. 1 illustrates a front view of a work space apparatus 100 for performing scientific analyses, such as chromatography. The work space apparatus 100 can include a top section 200 and a bottom section 300. The height of the top section 200 is denoted by $H_{top}$ and the height of the bottom section 300 is denoted by $H_{bottom}$ as illustrated in FIG. 1. In various implementations, the top section 200 can include a top surface 210, two side surfaces 220A, 220B and a desk surface 230. The work space apparatus 100 can incorporate a plurality of vertical supports or braces 222. The width of the top surface 210 is denoted by L in the horizontal direction x as illustrated in FIG. 1. The desk surface 230 may have a width dimension that is the same, longer, or shorter as the width L of the top surface 210. Generally, the desk surface 230 is arranged near a typical user's waist while standing and the bottom section 300 is arranged below a typical user's waist while standing such that the top section 200 provides a work region for the user.

Generally, the work space apparatus 100 is sturdy, maneuverable and has a compact footprint that allows the work space apparatus 100 to be used and easily maneuvered such as within a laboratory having other large equipment, in a laboratory refrigerator, or in a cold room where space is at a premium. In some implementations, the work space apparatus 100 can be at least about 42 inches, 44 inches, 46 inches, 48 inches, or up to about 50 inches in width (in the horizontal direction x). This narrow footprint provides for optimum flexibility within a small work space. The work space apparatus 100 can be at least about 50 inches, 52 inches, 54 inches, 56 inches, or up to about 58 inches in height (in the vertical direction y) and at least about 32 inches, 34 inches, 36 inches, 38 inches, or up to about 40 inches in depth (in the depth direction z). Generally, the materials and dimensions of the work space apparatus 100 are sufficient to support the various components used during experimental analyses, such as liquid chromatography. It should be appreciated that the dimensions provided herein are examples and that other dimensions for the work space apparatus 100 are within the scope and spirit of the present disclosure.

Again with respect to FIG. 1, the vertical braces 222, the top surface 210, the two side surfaces 220A, 220B and the desk surface 230 encloses a space that can be divided into columns 240A, 240B, 240C of smaller, independent modular spaces or a plurality of modules 250. Each column 240A, 240B, 240C can include a left sidewall 242 and a right sidewall 243. In some implementations, the right sidewall 243 of one column (e.g. 240A) forms the left sidewall of an adjacent column (e.g. 240B). The columns 240 can be further divided into rows forming the plurality of modules 250. The plurality of modules 250 can be coupled to the desk surface 230 and the top surface 210 can be coupled to and vertically above the plurality of modules 250. As will be described in more detail below, the height of modules 250 can be adjusted and customized to a user's needs. The plurality of modules 250 can be configured to support one or more components of an analytical system, such as a chromatography system. For example, if the analytical system is a chromatography system, each module 250 can be configured to receive one or more components of the chromatography system including, but not limited to, the valve modules and components, the air sensor modules and components, the pump and mixer modules and components, etc. Further, the top surface 210 provides a location for supporting an autosampler and related components such as the carousel, sampler, pump, robotic arms, well plates and trays, etc. In some implementations, a first plurality of modules 250 can receive a plurality of loading pumps (e.g. 2, 3, 4, or more), a second plurality of modules 250 can receive a plurality of eluting pumps (e.g. 2, 3, 4, or more), and a third plurality of modules 250 can receive a plurality of degassers (e.g. 2, 3, 4, or more). Further modules 250 can be configured to receive a valve interface module or other component or tools used during an analysis. This allows for the customization and personalization of the work space apparatus 100 pertinent to the particular analysis desired as well as the application and throughput needs of a user to increase functionality and automation of the system.

Generally, the apparatus 100 can include between 10 and 25 modules however, it should be appreciated that the number of modules 250 can vary. Any of a variety of combinations of columns and rows of modules 250 is considered herein. In some implementations, the work space apparatus 100 includes fifteen modules 250 divided into, for example, three columns 240A, 240B, 240C of five modules 250, stacked in a vertical direction y (i.e., in height) in each of the three columns 240A, 240B, 240C. In other implementations, the apparatus 100 can include three columns 240A, 240B, 240C of four modules 250. It should also be appreciated that the plurality of modules 250 need not be divided into three columns and can have fewer or more than three columns.

Again with respect to FIG. 1, each of the modules 250 allow for components of an analytical system, such as a chromatography system, to slide in and out of the column 240 in the depth direction z. The modules 250 can be forward-facing such that they provide easy access for insertion of a system component within the space of the module 250 in the depth direction z. The modules 250 can also be open on a back side such that the system component contained within the interior volume of the module 250 may be accessed such as for maintenance, connections, or other purposes. The plurality of modules 250 allow for compact stacking of the various system components such that they need not be stacked directly in contact with one another. This allows for easier access and maintenance of the various components in that they are removable and accessible independent of one another.

Figure 7:
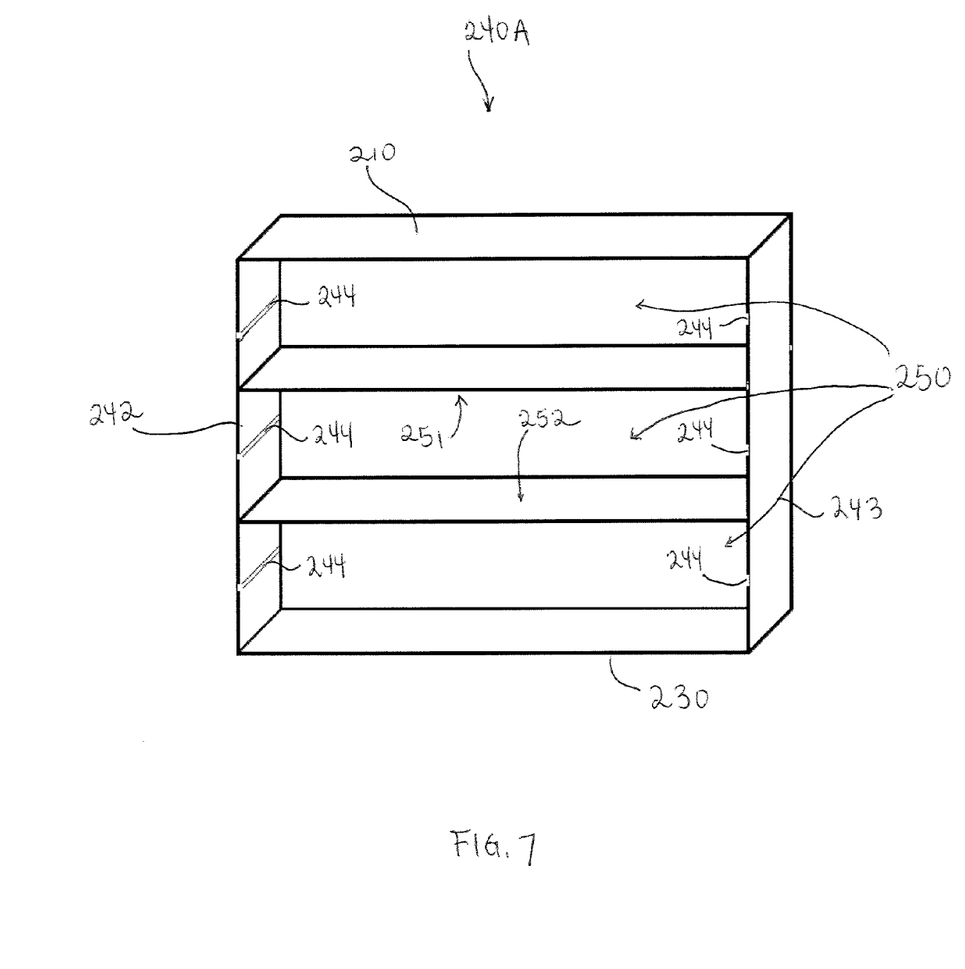
FIG. 7 illustrates a perspective view of an implementation of a plurality of modules.
Figure 8:
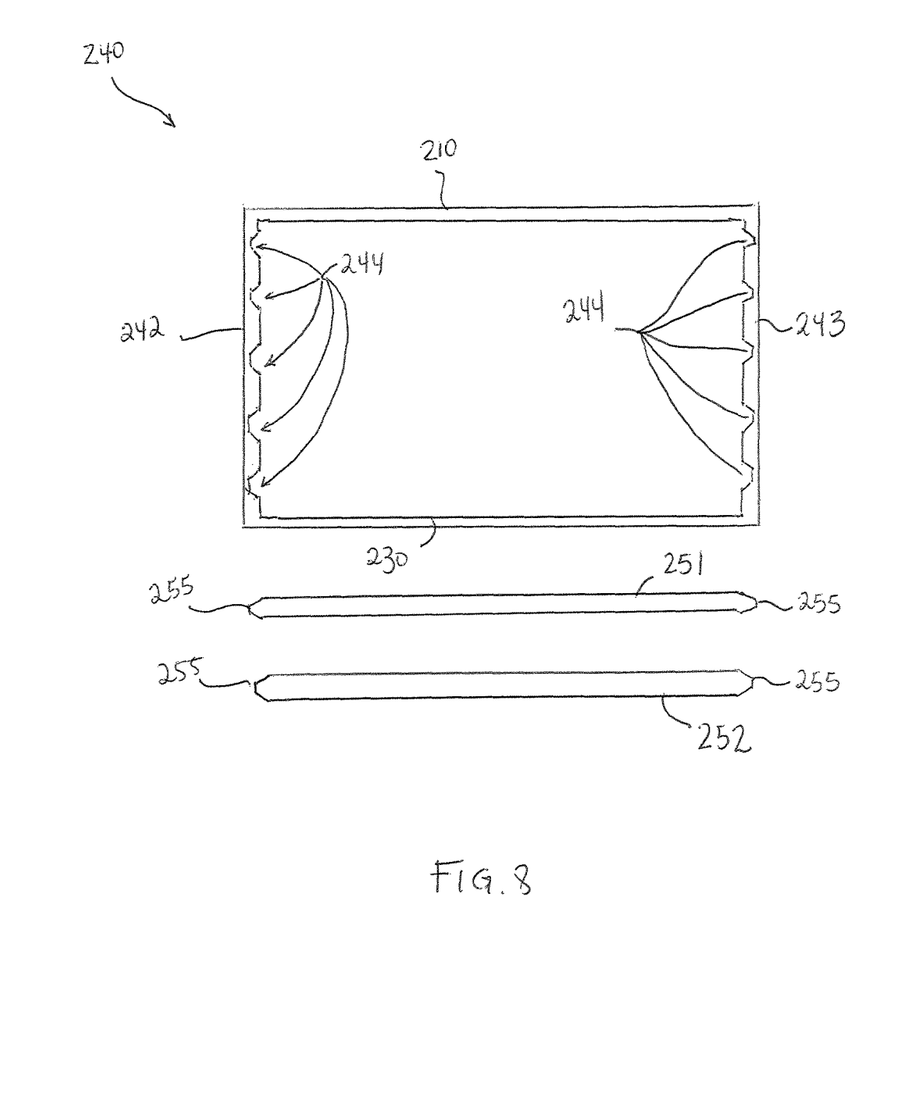
FIG. 8 illustrates an exploded, front view of the plurality of modules in FIG. 7.

Each of the plurality of modules 250 has a width defined by a first sidewall and a second sidewall as well as a height $H_{module}$. As mentioned above, the height $H_{module}$ of each of the plurality of modules 250 can be adjustable for customization of the work space apparatus 100. As an example, columns 240A, 240B, 240C can include a left sidewall 242 and a right sidewall 243 extending between the top surface 210 and the desk surface 230. The left sidewall 242 can include a groove 244 on a surface facing the right sidewall 243 and the right sidewall 243 can include a groove 244 on a surface facing the left sidewall 243 (see FIG. 1). The grooves 244 can extend from a front side of the apparatus 100 towards a back side of the apparatus 100 in the depth direction z. The grooves 244 of the left sidewall 243 and the grooves 244 of the right sidewall 243 form pairs of grooves 244 configured to receive a shelf board 251, 252. Thus, the internal space of one module 250 can be defined by a left sidewall 243, a right sidewall 243, a top shelf board 251 (or top surface 210) and a bottom shelf board 252 (or desk surface 230). The distance between the shelf boards 251, 252 defines the $H_{module}$. It should be appreciated however, that the desk surface 230 can form a lower surface of at least one of the modules 250 and that the top surface 210 can form an upper surface of at least one of the modules 250. It also should be appreciated that a top shelf board 251 of a first module 250 may be a bottom shelf board 252 of a second adjacent module 250 located above the first module 250. At least one of the shelf boards 251, 252 are removable from the apparatus. Each shelf board 251, 252 can have a first edge or a first slide element 255 extending outward from a left side edge and a second edge or a second slide element 255 extending outward from a right side edge (best shown in FIGS. 7-8). The edges or slide elements 255 are sized and shaped to be received within the corresponding groove 244 such that the shelf board 21, 252 can slide in the depth direction z. The slide elements 255 can be sized to insert within the corresponding pair of opposing grooves 244 of the sidewalls 242, 243 such that the slide element 255 on the left side mates with one or more grooves 244 on the left sidewall 242 and the slide 255 on the right side mates with one or more grooves 244 on the right sidewall 243. The opposing pair of grooves 244 of the sidewalls 242, 243 (i.e. the grooves positioned directly opposite one another within a particular module) and the corresponding pair of slide elements 255 can function like a drawer slide to provide smooth sliding movement relative to one another. The mating of the slide elements 255 with the grooves 244 on the left sidewall 242 and the right sidewall 243 provides structural support forming a module 250 within its respective column 240A, 240B or 240C. The mating of the module slide elements 255 with the grooves 244 on the left sidewall 242 and the right sidewall 243 can enhance the shelf boards to slide in and out of the column 240 in the depth direction z. The slide elements 255 and corresponding grooves 244 can have a variety of corresponding shapes such that they can slide relative to one another, including but not limited to square, rounds, oval, triangular, rectangular, dovetail, or polygonal shapes. In some implementations, the sidewalls 242, 243 rather than having grooves 244 can incorporate a projection configured to mate with a groove within the edge of the shelf boards 251, 252. Although the shelf boards are described herein as being slidingly removable into and out from the first and second grooves 244, it should be appreciated that any of a variety of mating configurations between the shelf boards 251, 252 and the sidewalls 242, 243 is considered herein. It should also be appreciated that the modules 250 may be stationary spaces or openings within the space defined by the top surface 210, the two side surfaces 220A, 220B and the desk surface 230, and may or may not include slide elements 255.

The modules 250 in the work space apparatus 100 need not be uniform in module height $H_{module}$. The modules 250 in the work space apparatus 100 can be adjusted to have different module heights $H_{module}$ depending on the respective placements of the top shelf board 251 and the bottom shelf board 252 relative to the grooves 244 for each of the modules 250. This allows for the work space apparatus 100 to support disparate components of varying heights such that they can be used together for a single analysis and arranged in practically any way a user desires. In some implementations, the grooves 244 are spaced in height along vertical direction y from each other by at least about 0.1 inch, 0.2 inch, 0.25 inch, 0.3 inch, 0.35 inch, 0.4 inch, 0.45 inch, 0.5 inch, up to about 1.0 inch. Smaller increments and increased number of groove pairs 244 increases the flexibility in height adjustments that can be made within each column 240. It should be appreciated that the distance the grooves 244 are spaced apart from one another along their respective sidewall 242, 243 can vary depending on the amount of customization in height of the modules 250 that is desired. Generally, the width of the modules 250 is fixed although it should be appreciated that the widths can be adjustable.

The modules 250 can include a door covering 253 (shown in FIG. 2), which may retract underneath the top surface 210 and may extend down to cover and/or protect one or more modules 250. Various configurations of the door covering 253 are considered herein. For example, one or more columns 240A, 240B, 240C can include its own door covering 253 that extends down to cover each of the modules 250 in that column. Alternatively, a single door covering 253 can extend the width dimensions of the three columns 240A, 240B, 240C to cover the modules 250 within all three columns 240A, 240B, 240C. In some aspects, a door covering 253 can also be included on the back side of the work space apparatus 100.

The work space apparatus 100 can further include a utility tray 350. In use, the utility tray 350 can be sized to receive one or more bottles of solvents, buffers, or other solution reservoirs typically used for chromatography analyses. The sides of the utility tray 350 can be sized to form a depth $D_{utility}$ sufficient to catch and hold spilled liquid within the utility tray 350. The utility tray 350 can be made of stainless steel or another material suitable for holding any residual liquids. The utility tray 350 can be positioned on the desk surface 230, for example, behind the plurality of modules 250. The utility tray 350 can be an extension of the desk surface 230 such that the bottom surface of the utility tray 350 is a portion of the desk surface 230. Alternatively, the utility tray 350 can include a bottom surface 351 that is separate from the desk surface 230. The utility tray 350 can be attached and/or detached from the desk surface 230. In some implementations, the utility tray 350 can be held in its place on the desk surface 230 by one or more fastening mechanisms, including, but not limited to, mechanical fasteners, adhesive fasteners, screws, nails, tapes, etc. In some implementations, one or more extension mechanisms can be coupled to the utility tray 350 to allow movement of the utility tray 350 relative to the desk surface 230. For example, using the extension mechanism(s) the utility tray 350 may move in one or more of the following directions: the horizontal direction x, the vertical direction y and/or the depth direction z relative to the desk surface 230. This allows for a user to move the utility tray 350 out from behind the plurality of modules 250, for example, to access the liquid buffer reservoirs such as to replace, fill, or make connections, without interference by the components housed within the plurality of modules 250.

Figure 2:
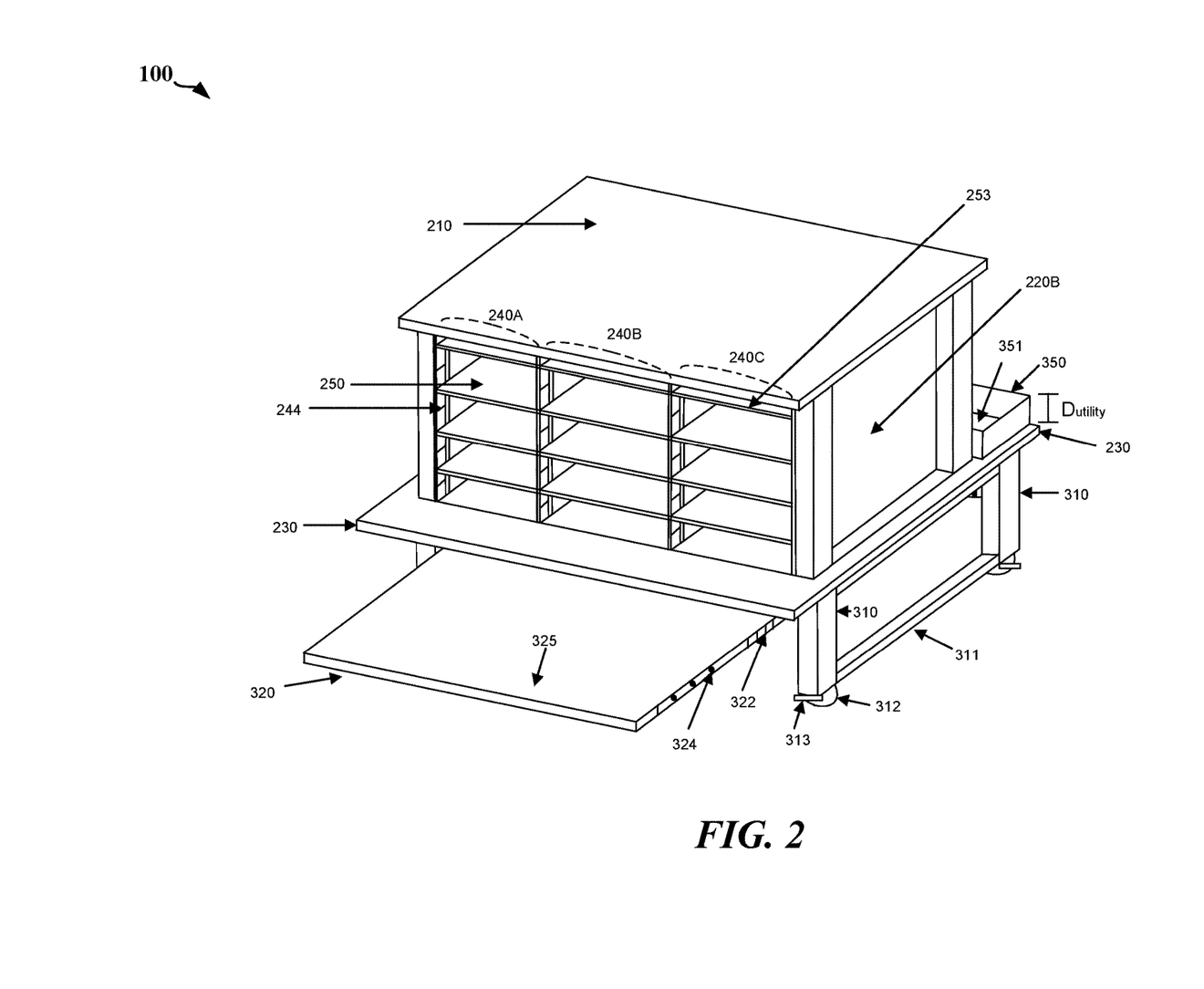
FIG. 2 illustrates a perspective view of the work space apparatus of FIG. 1.

The bottom section 300 provides support to the top section 200 such that the work space apparatus 100 can be used independently without the need for a surface to place the plurality of modules 250. The bottom section 300 can include one or more lower supports, pedestals or leg posts 310 configured to support the top section 200 in a sturdy and stable manner. In some implementations, the bottom section 300 includes four leg posts 310 with each leg post 310 attached at or near each of the four corners of the desk surface 230. The work space apparatus 100 can be mobile and mounted on swiveling casters 312 for rolling the work space apparatus 100. One or more of the casters 312 can include a wheel lock 313 to keep the work space apparatus 100 in a stationary location after it is moved. The casters 312 are shown in FIG. 2 in the locked position with the wheel locks 313 engaged. The bottom section 300 can also include one or more crossbars 311 extending between pairs of leg posts 310 to provide further support to each of the leg posts 310 allowing the work space apparatus 100 to bear greater loads. It should be appreciated that any of a variety of supports for the top section 200 is considered herein although the bottom section 300 is generally configured to stably support loads typical of laboratory equipment, such as for chromatography.

The bottom section 300 can also include one or more pullout desktops or shelves 320 located under the desk surface 230. The pullout shelf 320 can be in a stowed position (as shown in FIG. 1) in which its components are stowed within the width dimension (in the horizontal direction x) and the depth dimension (in the depth direction z) of the work space apparatus 100. The pullout shelf 320 can be in a pulled out position (as shown in FIG. 2) in which the pullout shelf 320 extends beyond the desk surface 230 in the depth direction z. As best shown in FIG. 2, the pullout shelf 320 can include an upper surface forming a shelf component 325 configured for various tasks such as writing, typing, or holding tools and equipment for the particular analyses being performed. The pullout shelf 320 can also include left and right side surfaces having a pair of track housings 322 and a pair of tracks 324 attached. The pair of tracks 324 can slide within the pair of track housings 322 to allow the pullout shelf 320 to slide under the desk surface 230 (i.e., stowed position) and to pull out and fully extend beyond the desk surface 230 (i.e., pulled out position). As mentioned above, the utility tray 350 can be configured to move relative to the desk surface 230. In some implementations, the pullout shelf 320 is positioned near a front side of the apparatus 100 and the utility tray 350 is positioned near a back side of the apparatus 100 such that the pullout shelf 320 can extend in a direction that is 180 degrees from the direction in which the pullout shelf 320 extends beyond the desk surface 230. That is, the pullout shelf 320 may extend in a first direction beyond at least one dimension of the desk surface 230 and the utility tray 350 is coupled to the desk surface in a second direction, wherein the first direction and the second direction are in opposite directions from each other. It should be appreciated that each of the pullout shelf 320 and the utility tray 350 can be moved in various directions relative to the desk surface 230.

Figure 3:
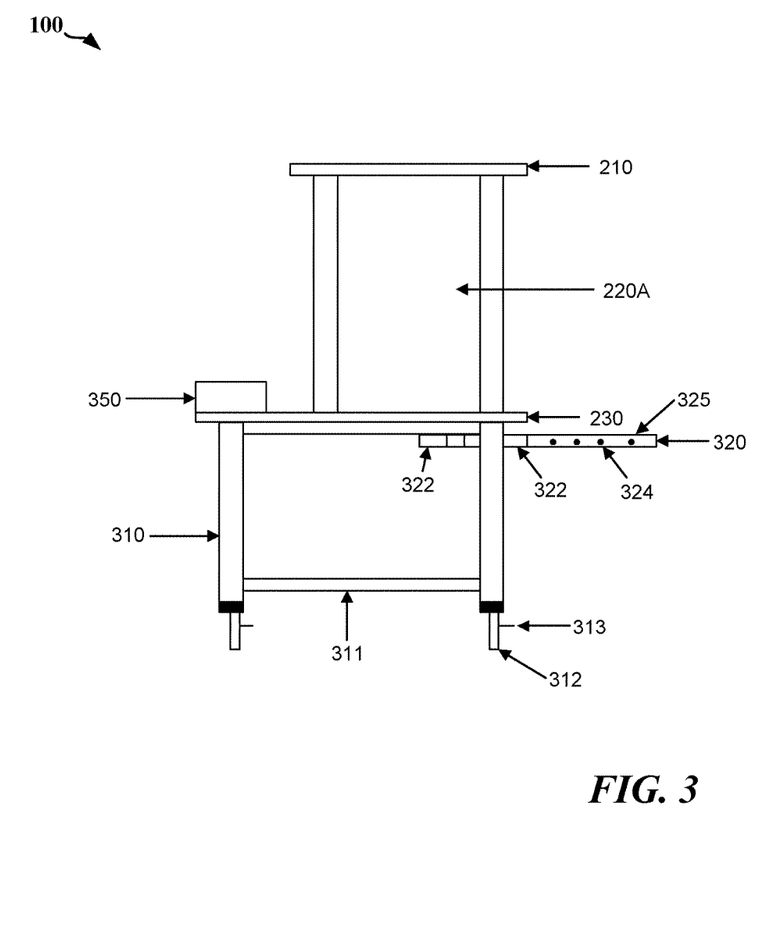
FIG. 3 illustrates a left side view of the work space apparatus of FIG. 1.

FIG. 3 illustrates a left side view of the example work space apparatus 100 of FIG. 1. As illustrated in FIG. 3, the pullout shelf 320 is in the pulled out position. The casters 312 are shown in the locked position with the wheel locks 313 engaged. As shown in FIG. 3, in some implementations, the pullout shelf 320 may have dimensions that are smaller than the dimensions of the desk surface 230. For example, in the stowed position, the pullout shelf 320 may be completely stowed underneath the desk surface 230.

Figure 4:
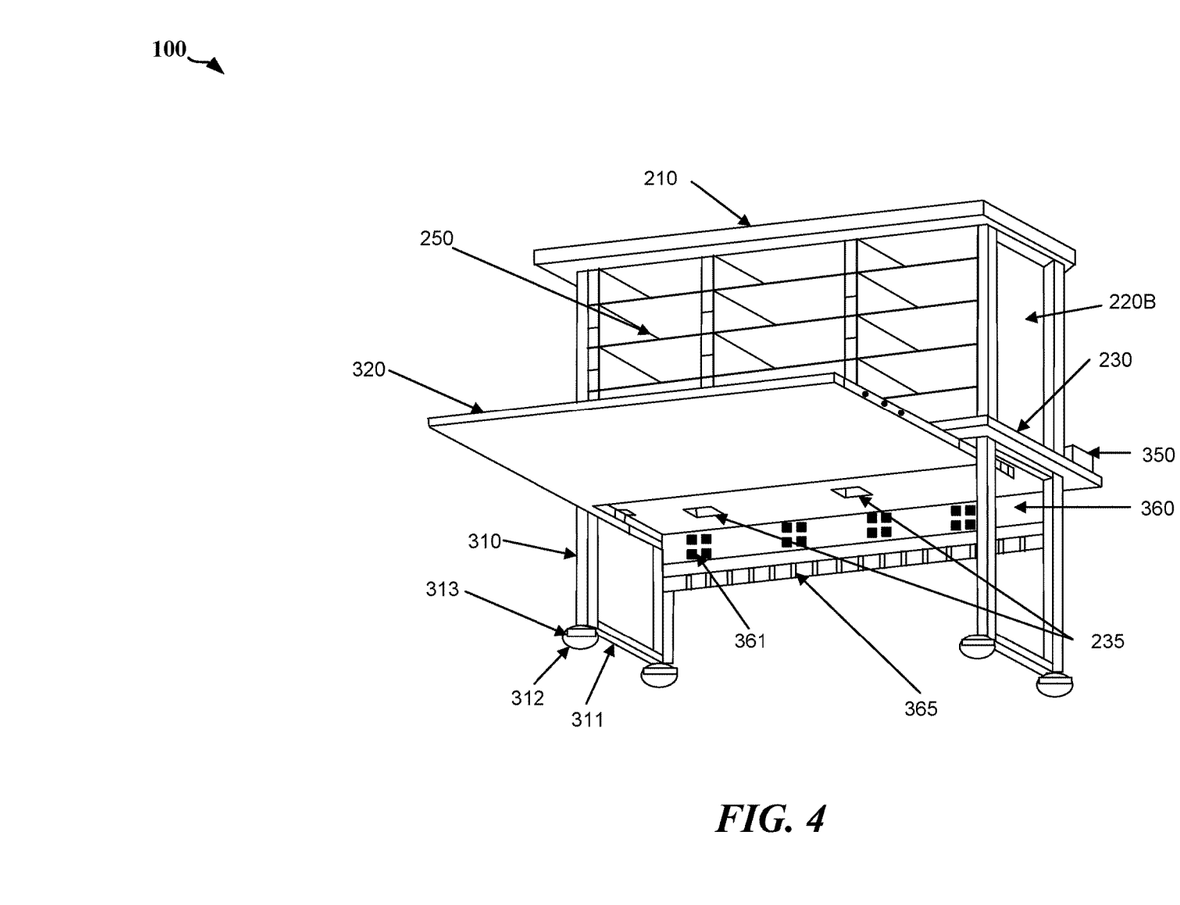
FIG. 4 illustrates a perspective bottom view of the work space apparatus of FIG. 1.

FIG. 4 illustrates a perspective bottom view of the example work space apparatus 100 of FIG. 1. In some implementations, the work space apparatus 100 can include one or more power sockets 361. Shown in FIG. 4 is an electrical panel 360 extending in a downward vertical direction from the desk surface 230. It should be appreciated that the location of the electrical panel 360 can vary and can be located elsewhere on the work space apparatus 100. The one or more power sockets 361 can be part of the electrical panel 360 such that the one or more power sockets 361 are housed by the electrical panel 360. The electrical panel 360 can house one or more power supplies (not shown) for powering the one or more power sockets 361, and/or one or more power electronic units (not shown) for use in the scientific analysis. Vent holes 365 (shown in FIGS. 1 and 4) can extend from the electrical panel 360 for dissipating heat, for example, from the one or more power supplies and/or one or more power electronic units.

Figure 5:
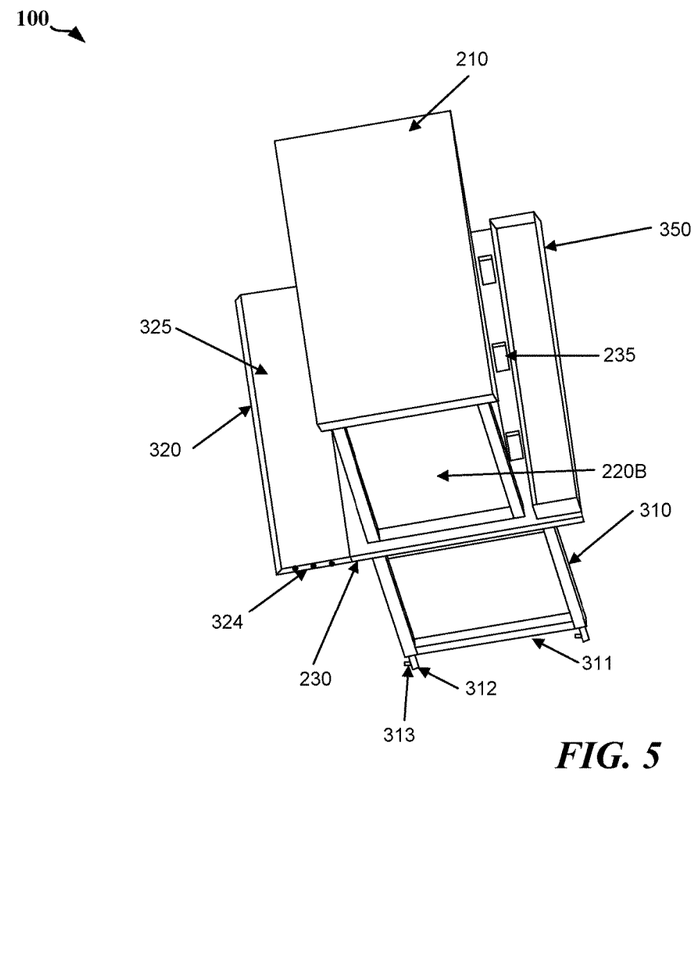
FIG. 5 illustrates a perspective top view of the work space apparatus of FIG. 1.

FIGS. 4-5 show one or more cutouts 235 on the desk surface 230. In some implementations, the cutouts 235 can facilitate electrical connections of any equipment placed within the modules 250, any equipment placed on the top surface 210, and/or any equipment placed within the utility tray 350 to the one or more power sockets 361. Although the figures show three cutouts 235, it should be appreciated the work space apparatus 100 can include fewer or more than three cutouts 235 as well as no cutouts 235.

Figure 6:
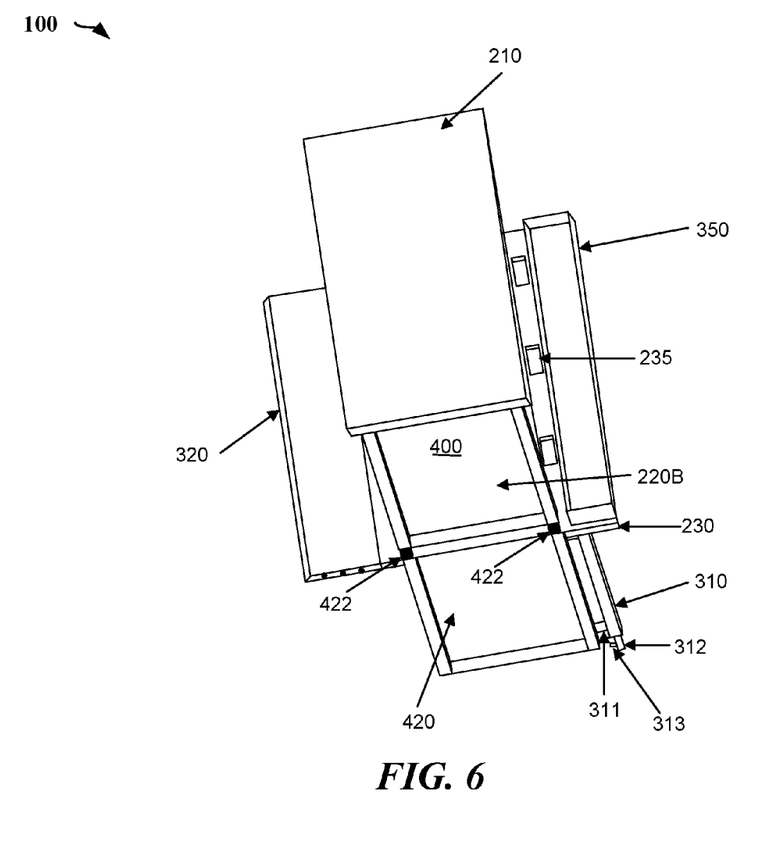
FIG. 6 illustrates a perspective top view of the work space apparatus of FIG. 1 with a screen monitor.

Now with respect to FIG. 6, the work space apparatus 100 can be configured to couple with a screen monitor 400. The screen monitor 400 can be coupled to one or both of the two side surfaces 220A, 220B. The screen monitor 400 can be mounted by an adjustable mechanism such that the screen monitor 400 can be folded against the side surface or unfolded away from the side surface. The monitor 400 can be adjusted to face a front, side or back of the apparatus 100. It should be appreciated that the screen monitor 400 can be mounted such that is can be adjusted around one or more axes as is known in the art.

Still with respect to FIG. 6, the apparatus can further include one or more flip trays 420. The flip tray 420 can be hinged, for example around points 422, such that the flip tray 420 can rotate around the hinge up to 180 degrees from a plane orthogonal to the desk surface 230. As such, the flip tray 420 can serve as a protective covering to the screen monitor 400 when the flip tray 420 is placed in a parallel position to the right side surface 220B (e.g. rotated 0 degrees). The flip tray 420 can also serve as an additional extended surface to the work space apparatus 100 when the flip tray 420 is placed in a horizontal position (e.g. rotated 90 degrees). In some implementations, the points 422 are part of the desk surface 230 such that the flip tray 420 is hinged to the desk surface 230. Mechanical hinges or fasteners can be included at the points 422 to allow the flip tray 420 to be placed from the horizontal position to the parallel position and vice versa. In some examples, the hinges can allow the flip tray 420 to be placed in a vertically downward position adjacent to the leg posts 310 (e.g. rotated 180 degrees as shown in FIG. 6). The stowing of the flip tray 420 either in a parallel position to the right side surface 220B or in the vertically downward position adjacent to the leg posts 310 allows a more compact configuration for the work space apparatus 100.

Although only one screen monitor 400 is illustrated in FIG. 6, it should be appreciated that a second screen monitor may be housed on the left side surface 220A. Also, a second flip tray 420 may be included at the left side surface 220A. Further, the screen monitor 400 can be arranged such that the work space apparatus 100 is configured to be a "left-hand" instrument or a "right-hand" instrument with respect to the location of the detector device, such as the mass spectrometer, and the arrangement of equipment in the laboratory within which the apparatus 100 is to be used.

In various examples, the work space apparatus 100 may include various types of fasteners (including but not limited to magnetic surfaces, adhesives, hooks, clamps, clips, or other feature) for attaching to various components, such as but not limited to, a keyboard, a mouse, etc. For example, the fasteners may be found in one or more of the following: the flip tray 420, one or more leg posts 310, the top surface 210, the desk surface 230, the pullout shelf 320, etc.

As described above, the vertical and horizontal arrangement of the plurality of modules 250 can support and organize the various components to be used for an analysis, such as a chromatography analysis, in a logical and efficient manner taking up relatively little workspace within the laboratory environment. The system components can be housed in close proximity to one another using the work space apparatus 100 allowing for the components to be coupled together forming an integrated system of components easily maneuvered, set-up and used with other equipment of the lab. In addition to the small footprint, the work space apparatus 100 described herein is manufactured of materials that are strong enough to support the weight of typical analytical equipment used in a laboratory setting and lightweight enough to be easily maneuvered. One or more elements of the work space apparatus 100 can be formed of any of a variety of materials including, but not limited to metal, steel, aluminum, plastic, wood, high pressure laminates, and wood-like composites as is known in the art.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. Use of the terms "front," "side," and "back" are used throughout the description for purposes of clarity and are not intended to be limiting. Such terms are provided to establish relative frames of reference, and are not intended to limit the use or orientation of an anchoring delivery system to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A work space apparatus for performing scientific analysis, comprising:
   a desk surface;
   a plurality of modules coupled to an upper region of the desk surface, wherein each of the plurality of modules has a width defined by a first sidewall and second sidewall and has a height that is adjustable;
   a utility tray having sides sized to form a depth sufficient to catch and hold spilled liquid within the utility tray, wherein the utility tray is coupled to the desk surface; and a top surface coupled to and vertically above the plurality of modules.

2. The work space apparatus of claim 1, wherein the height of each of the plurality of modules is defined by at least one first shelf board that is removable from the apparatus.

3. The work space apparatus of claim 2, wherein the first sidewall has at least a first groove and the second sidewall has at least a second groove, wherein the first groove and the second groove are positioned directly opposite one another forming a first pair of grooves.

4. The work space apparatus of claim 3, wherein the at least one first shelf board has a first edge that mates with the first groove in the first sidewall and a second edge that mates with the second groove in the second side wall.

5. The work space apparatus of claim 4, wherein the at least one first shelf board is slidingly removable from the first pair of grooves and slidingly insertable into a second pair of grooves, wherein the second pair of grooves is positioned in the first and second sidewall a distance above or below the first pair of grooves.

6. The work space apparatus of claim 1, further comprising a shelf coupled below the desk surface.

7. The work space apparatus of claim 6, wherein the shelf is a pullout shelf comprises a pair of tracks for stowing the pullout shelf beneath the desk surface and for extending the pullout shelf in a first direction beyond at least one dimension of the desk surface.

8. The work space apparatus of claim 7, wherein the utility tray is movable in a second direction, wherein the first direction and the second direction are in different directions from each other.

9. The work space apparatus of claim 1, further comprising an electrical panel extending vertically downward from the desk surface.

10. The work space apparatus of claim 1, wherein the desk surface comprises at least one cutout for facilitating an electrical connection of equipment placed within one of the plurality of modules.

11. The work space apparatus of claim 1, further comprising a screen monitor housed on a side surface of the work space apparatus.

12. The work space apparatus of claim 1, further comprising a lower support coupled to the desk surface, wherein the lower support is coupled to casters having a wheel lock.

13. The work space apparatus of claim 1, wherein the first sidewall includes a first groove formed therein, and the second sidewall includes a second groove formed therein, wherein the first groove and the second groove are positioned directly opposite one another.

14. The work space apparatus of claim 13, further comprising a shelf board defining a height of at least one of the plurality of modules, wherein the shelf board has a first edge that is complementarily receivable in the first groove in the first sidewall and a second edge that is complementarily receivable in the second groove in the second side wall, and wherein the shelf board is slidably movable within the first and second grooves.

* * * * *